United States Patent
Tegels

(10) Patent No.: US 10,555,719 B2
(45) Date of Patent: Feb. 11, 2020

(54) ULTRASOUND ASSISTED NEEDLE PUNCTURE MECHANISM

(71) Applicant: ST. JUDE MEDICAL PUERTO RICO LLC, Caguas, PR (US)

(72) Inventor: Zachary J. Tegels, Minneapolis, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 600 days.

(21) Appl. No.: 13/795,551

(22) Filed: Mar. 12, 2013

(65) Prior Publication Data
US 2014/0276081 A1 Sep. 18, 2014

(51) Int. Cl.
*A61B 8/00* (2006.01)
*A61B 8/08* (2006.01)
*A61B 17/34* (2006.01)

(52) U.S. Cl.
CPC ............ *A61B 8/085* (2013.01); *A61B 8/0841* (2013.01); *A61B 8/4209* (2013.01); *A61B 17/3403* (2013.01); *A61B 8/4444* (2013.01); *A61B 8/461* (2013.01); *A61B 2017/3413* (2013.01)

(58) Field of Classification Search
CPC ............................ A61B 8/4209; A61B 8/4444
USPC ........................................................ 600/461
See application file for complete search history.

(56) References Cited

U.S. PATENT DOCUMENTS

| | | | |
|---|---|---|---|
| 6,485,426 B2 * | 11/2002 | Sandhu | 600/461 |
| 6,529,764 B1 * | 3/2003 | Kato | A61B 5/055 324/318 |
| 2006/0229641 A1 * | 10/2006 | Gupta et al. | 606/130 |
| 2007/0106208 A1 * | 5/2007 | Uber, III | A61M 5/142 604/65 |
| 2008/0114305 A1 * | 5/2008 | Gerondale | A61M 5/31555 604/207 |
| 2008/0300491 A1 * | 12/2008 | Bonde et al. | 600/461 |
| 2012/0259220 A1 * | 10/2012 | Sheldon et al. | 600/439 |
| 2012/0330159 A1 * | 12/2012 | Orome | A61B 8/0841 600/461 |
| 2013/0116708 A1 * | 5/2013 | Ziniti | A61B 17/0485 606/144 |

* cited by examiner

*Primary Examiner* — Jonathan Cwern
(74) *Attorney, Agent, or Firm* — Dorsey & Whitney LLP

(57) ABSTRACT

A tissue puncture assembly includes an ultrasound probe, a tissue puncture device, and an adjustment device. The ultrasound probe includes a probe end arranged to contact a tissue surface, the ultrasound probe being operable to determine a depth of a body cavity positioned below the tissue surface. The tissue puncture device is configured to penetrate the tissue surface to gain access to the body cavity. The adjustment device is mounted to the ultrasound probe and operable to adjust an orientation of the tissue puncture device relative to the ultrasound probe.

19 Claims, 13 Drawing Sheets

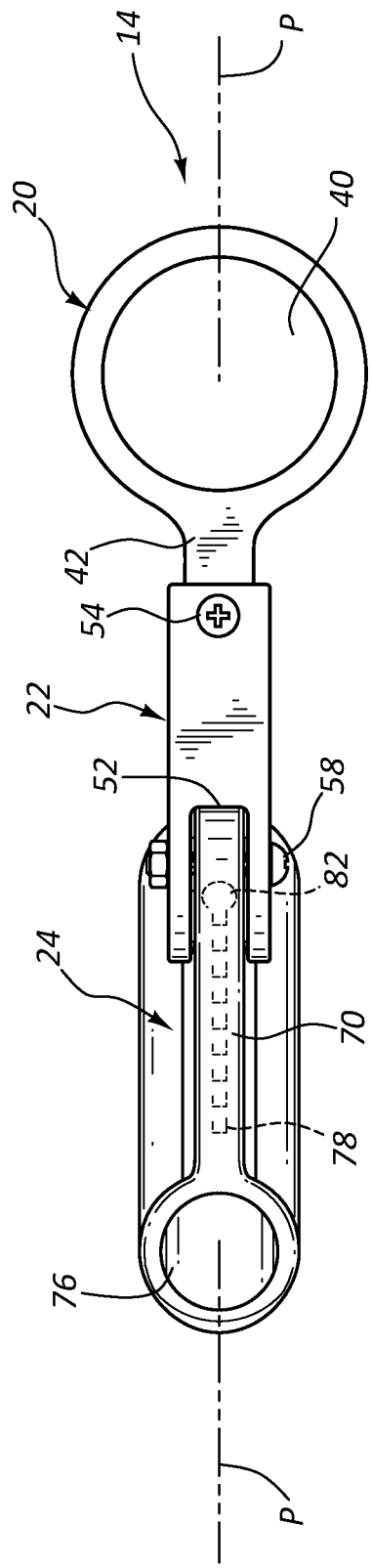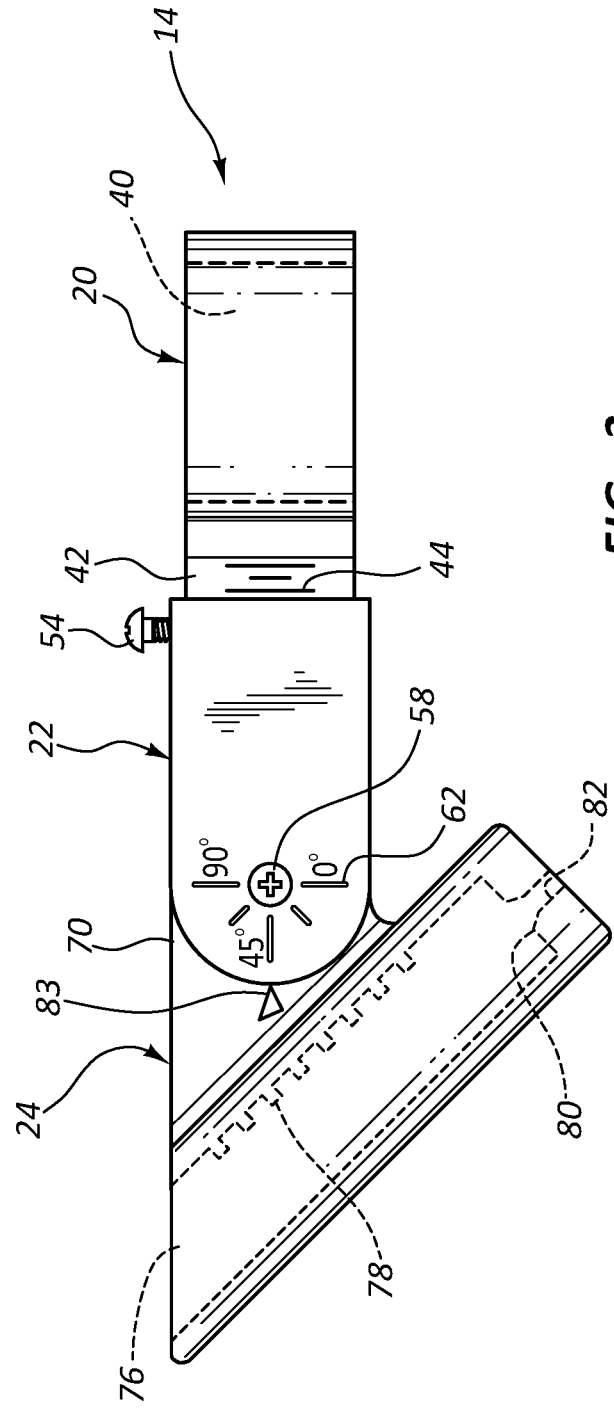

ULTRASOUND ASSISTED NEEDLE PUNCTURE MECHANISM

TECHNICAL FIELD

The present disclosure relates generally to medical procedures, and more particularly, to systems and methods for locating and accessing vessels percutaneously.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Challenges exist related to locating the artery prior to inserting a needle or other device used to create the percutaneous puncture and access the artery. Typically, the artery is positioned below a layer of tissue at an unknown distance from an outer surface of the patient. Further, the shape and size of the artery and an orientation of the artery may vary at different locations on a patient. Additionally, the operator may wish to insert the needle or other device being used to create the percutaneous puncture at a certain angle relative to a longitudinal axis of the artery or at a specific location around a circumference of the artery. Some or all of these considerations may create a need for improved systems and methods for locating and accessing vessels percutaneously.

SUMMARY

One aspect of the present disclosure relates to a tissue puncture assembly having an ultrasound probe, a tissue puncture device, and an adjustment device. The ultrasound probe includes a probe end arranged to contact a tissue surface, the ultrasound probe being operable to determine a depth of a body cavity positioned below the tissue surface. The tissue puncture device is configured to penetrate the tissue surface to gain access to the body cavity. The adjustment device is mounted to the ultrasound probe and operable to adjust an orientation of the tissue puncture device relative to the ultrasound probe.

The adjustment device may include an adjustable length to vary a distance between the ultrasound probe and the tissue puncture device. The adjustment device may include a pivot adjustment portion operable to change an angle or orientation of the tissue puncture device relative to the ultrasound probe. The tissue puncture assembly may include a display configured to show a position of the ultrasound probe and tissue puncture device relative to the body cavity. The tissue surface may be an outer skin surface of a patient, and the body cavity may be a vessel lumen.

The tissue puncture device may include a hub and a puncture member mounted to the hub, wherein the hub is adjustably mounted to the adjustment device. The tissue puncture assembly may include a stabilizing member extending radially outward from the ultrasound probe and being arranged to contact the tissue surface. The stabilizing member may include a circular shaped ring portion arranged to contact the tissue surface. The stabilizing member may be adjustable along a length of the ultrasound probe. The ultrasound probe, tissue puncture device, and adjustment device may be arranged in a common plane.

Another aspect of the present disclosure relates to a needle placement assembly that includes an ultrasound probe, a needle, and a needle adjustment device. The needle adjustment device may include a probe attachment member connected to the ultrasound probe, and a needle carrier connected to the needle and adjustably mounted to the probe attachment member to adjust a position of the needle relative to the ultrasound probe.

The needle may be movable relative to the needle carrier and insertable through a surface of a tissue layer against which the ultrasound probe abuts. The ultrasound probe may be configured to abut against a tissue layer and locate a vessel positioned below the tissue layer, wherein the needle may be insertable through the tissue layer and a sidewall of a vessel to access a lumen of the vessel. The needle placement assembly may include a display showing images of the vessel generated by the ultrasound probe. The needle adjustment device may include a length adjustment portion and a pivot adjustment portion.

A further aspect of the present disclosure relates to a method of accessing a vessel percutaneously. The method includes providing a needle placement assembly having an ultrasound probe, a needle adjustment device, and a needle, wherein the ultrasound probe and needle are mounted to the needle adjustment device. The method further includes contacting the ultrasound probe against a tissue layer, determining a location of the vessel below the tissue layer, adjusting the needle adjustment device to alter an orientation of the needle relative to the ultrasound probe, and advancing the needle through the tissue layer and into the vessel.

Determining a location of the vessel may include displaying images of the vessel and tissue layer on a display screen. Adjusting the needle adjustment device may include adjusting at least one of a length and a rotated position of the needle adjustment device. The needle adjustment device may include a probe attachment member connected to the ultrasound probe, a needle carrier connected to the needle, and an adjustment member, and adjusting the needle adjustment device may include adjusting at least one of a distance and a rotated position of the probe attachment member relative to the needle carrier with the adjustment member. The method may further include providing a stabilization ring, mounting the stabilization ring to one of the ultrasound probe and the needle adjustment device, and contacting the stabilization ring against the tissue layer after determining a location of the vessel.

The foregoing and other features, utilities, and advantages of the invention will be apparent from the following detailed description of the invention with reference to the accompanying drawings.

BRIEF DESCRIPTION OF THE DRAWINGS

The accompanying drawings illustrate various embodiments of the present disclosure and are a part of the specification. The illustrated embodiments are merely examples of the present disclosure and do not limit the scope of the invention.

FIG. 3 is a side view of a needle adjustment device of the needle placement assembly of FIG. 1.

FIG. 4 is a top view of the needle adjustment device of FIG. 3.

Throughout the drawings, identical reference numbers designate similar, but not necessarily identical, elements.

DETAILED DESCRIPTION

Figure 1:
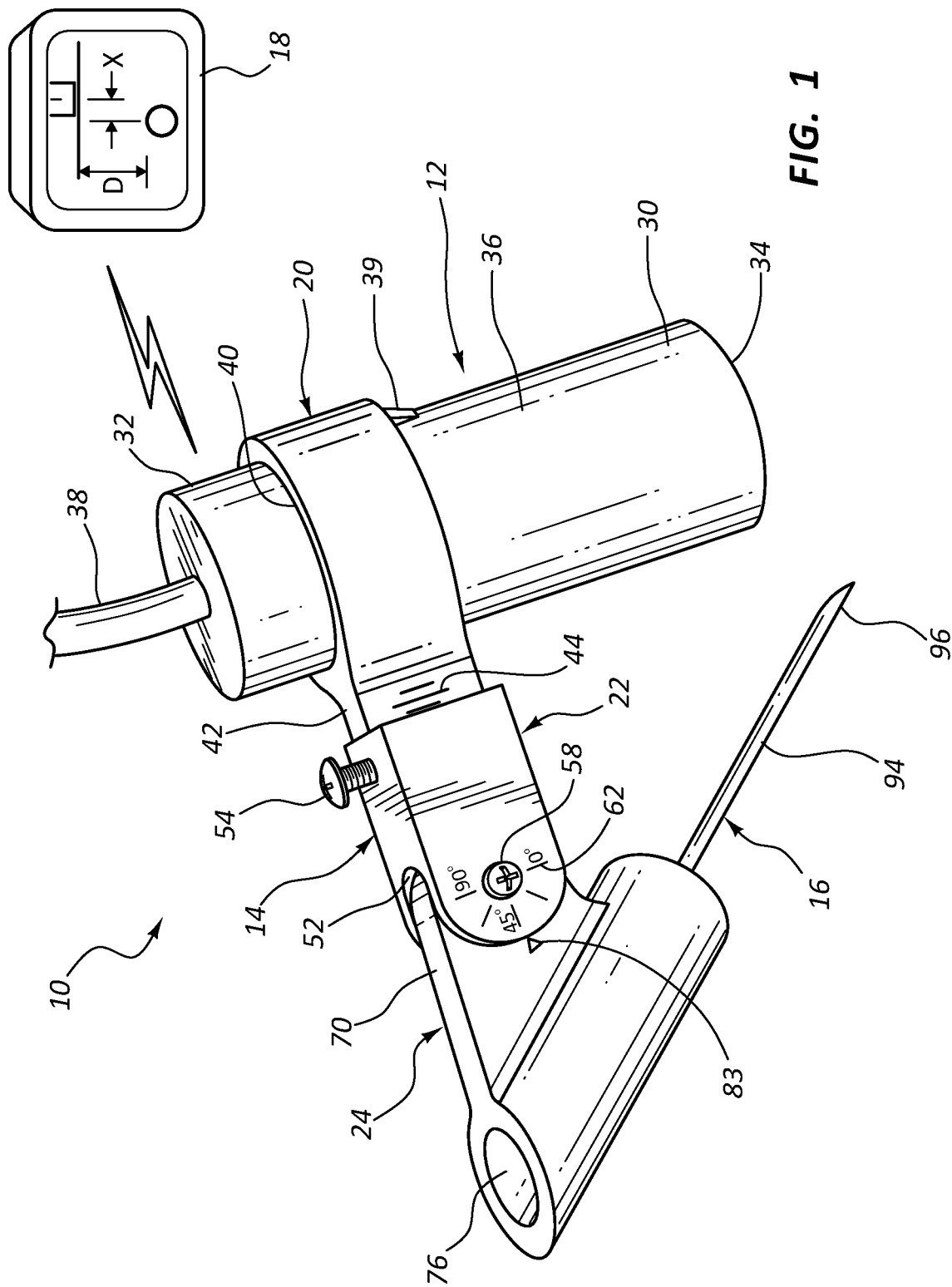
FIG. 1 is a perspective view of an example needle placement assembly in accordance with the present disclosure.
Figure 2:
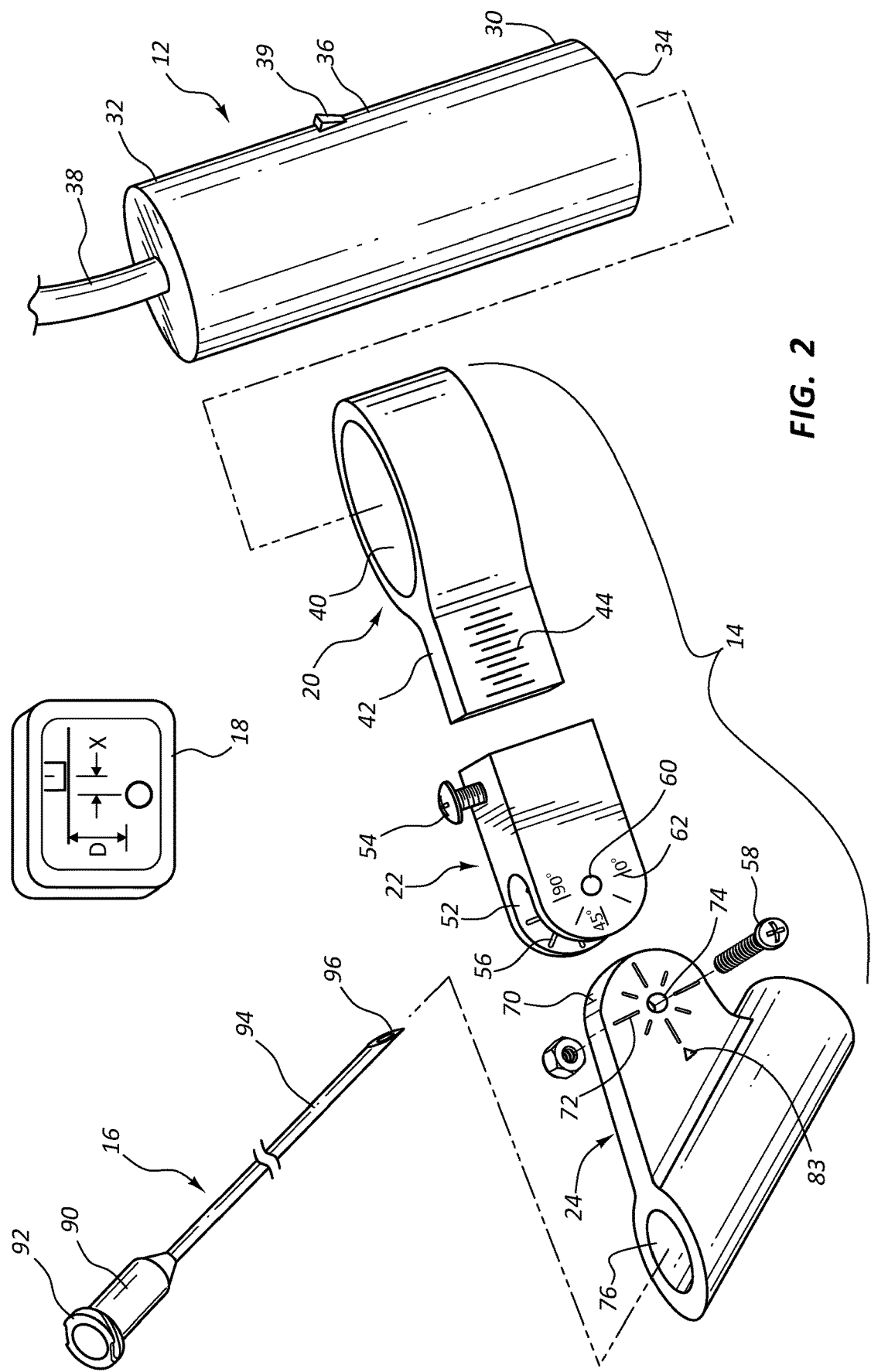
FIG. 2 is an exploded perspective view of a needle placement assembly of FIG. 1.

The systems and methods disclosed herein may be used to locate a body cavity and form percutaneous punctures through a body layer of a patient to gain access to the body cavity. Access through a percutaneous puncture allows a physician to carry out various procedures in or through the body cavity for examination, surgery, treatment and the like. While not meant to be limiting, the systems are illustrated being used to locate a blood vessel, such as a femoral artery, and for a percutaneous puncture in the blood vessel in a patient. It will be appreciated that the systems, devices and methods are applicable to other procedures requiring through body tissue into a cavity including, for example, laparoscopic surgery and other microscopic surgery techniques using a relatively small incision. Applications of access systems and methods including those implementing principles described herein include locating a blood vessel and forming a percutaneous puncture or incision in tissue leading to a body cavity and through a wall of the body cavity, such as punctures or incisions in blood vessels, ducts or lumens, gall bladders, livers, hearts, etc.

As used in this specification and the appended claims, the terms "engage" and "engagable" are used broadly to mean interlock, mesh, or contact between two structures or devices. Likewise "disengage" or "disengagable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as well as their derivatives, as used in the specification, including the claims, have the same meaning as the word "comprising."

The systems and methods disclosed herein may provide a number of advantages related to locating and accessing a vessel percutaneously. One function of the systems and methods disclosed herein relates to centrally and accurately puncturing a vessel for vascular access with the assistance of ultrasound. An example system includes an attachment to an ultrasound probe, a sliding needle guide, and a needle adjustment feature. The device may connect to an ultrasound probe using, for example, a snap-fit connection, a press-fit connection, a fastener, or other type of secure attachment that limits movement between the ultrasound probe and the adjustment device. The adjustment device may be aligned with the ultrasound probe such that a needle puncture provided by the needle is oriented co-planar with the ultrasound probe and is readily visible through imaging provided by the ultrasound probe while accessing the vessel.

An example adjustment device, which may also be referred to as a needle adjustment device, may include a lateral adjustment feature that allows the device to be adjusted to achieve punctures of varying depth. The angle at which the puncture is oriented may be modified to obtained a puncture of a desired depth for a given fixed distance between the needle member and the ultrasound probe. The angular or pivotal adjustment of the device may be guided using a set of marks or indicators to provide a visual indication to the operator of the rotated position of the needle relative to the ultrasound probe. The needle guide of the device may permit the needle to be advanced through a tissue layer and into the vessel, which is positioned below an outer surface of the tissue layer. The needle may be advanced while monitoring a position of the needle using the ultrasound probe. After accessing the vessel with the needle, the needle member may be detached from the ultrasound probe and/or the adjustment device for future treatment procedures.

The needle guide may include, for example, a combination of biasing member and locking features to allow easier movement of the needle relative to the needle guide and the ability to lock the position of the needle (e.g., during penetration of the tissue layer to gain access to the vessel and after securing access into the vessel). As an alternative to detaching the needle from the needle adjustment device or the ultrasound probe, a portion of the needle guide may be detachable from remaining portions of the needle adjustment device to help maintain needle placement within the vessel after obtaining access.

The needle placement assembly may also include a stabilization member such as a stabilization ring, which helps maintain a desired position of the ultrasound probe. In one example, the stabilization member helps hold the ultrasound probe in a desired rotated, pivoted, and axial position relative to an outer skin surface against which the ultrasound probe abuts during use. The stabilization member may be brought into contact with the outer surface of the tissue layer only after the vessel has been located using the ultrasound probe. The stabilization member may hold the ultrasound probe in a desired orientation and position while advancing the needle to gain access to the vessel. In one example, the stabilization member is retractable along a length of the ultrasound probe so as not to interfere with movement of the ultrasound probe when locating the vessel. The stabilization member may include a high friction material at an interface with the outer surface of the tissue layer to help maintain a position of the stabilization member relative to the patient during advancement of the needle into the vessel.

Referring to FIGS. 1-5, an example needle placement assembly 10 is shown including an ultrasound probe 12, a needle adjustment device 14, a needle member 16, and a monitor or display member 18. The needle adjustment device 14 is mounted to the ultrasound probe 12. The needle member 16 may be insertable through and carried by the needle adjustment device 14. Images collected by the ultrasound probe 12 may be viewable on the monitor 18. The ultrasound probe 12 may operate to determine the location of a vessel below an outer surface of a tissue layer. In one example, the tissue layer includes an outer skin surface and the vessel is positioned within the tissue layer at a location below the outer skin surface. The ultrasound probe 12 may assist in determining a depth D of the vessel as well as a lateral spacing X between a central axis of the vessel and a central longitudinal axis of the ultrasound probe 12 (see FIG. 1).

Figure 5:
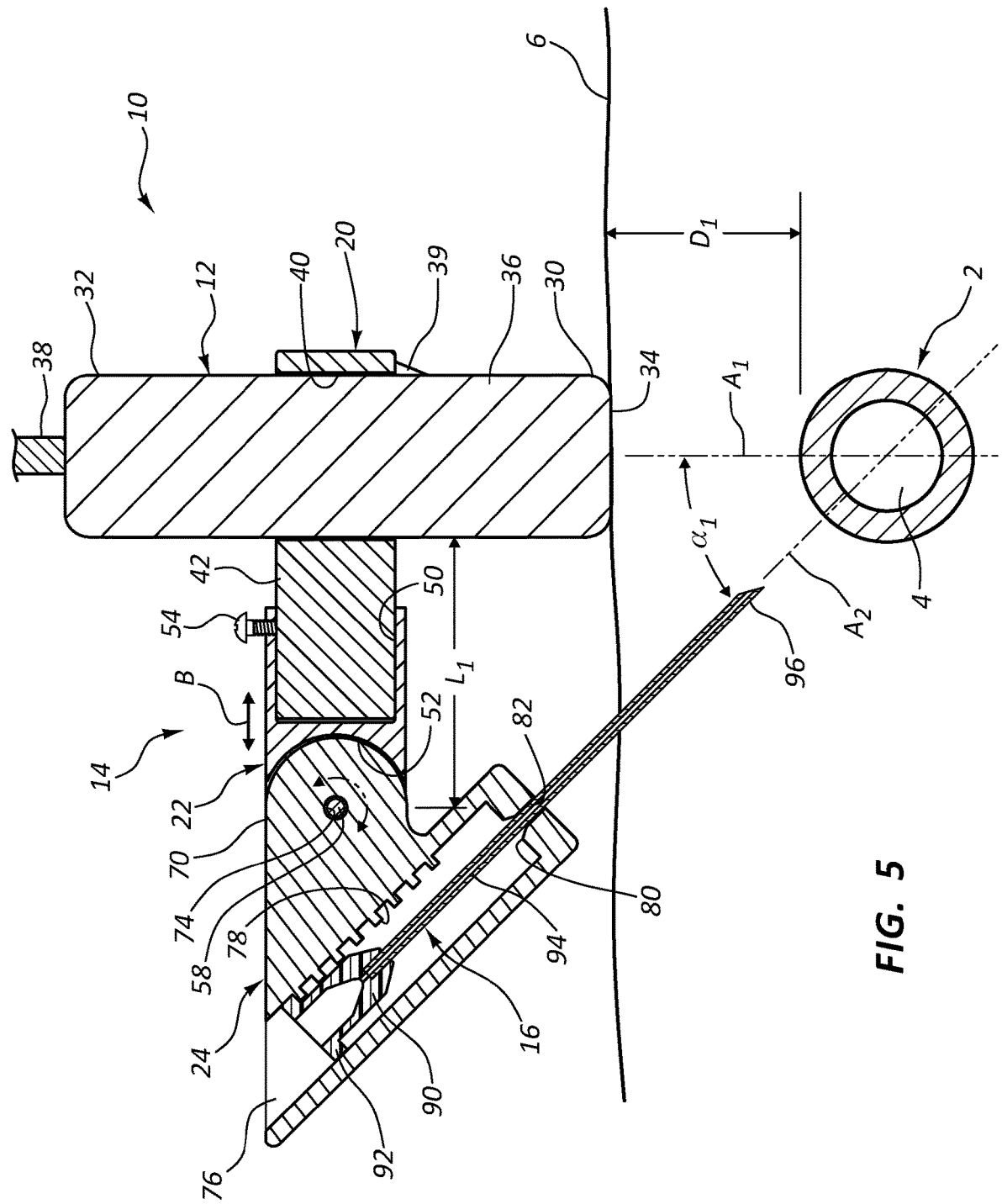
FIG. 5 is a cross-sectional view of the needle placement assembly of FIG. 1 in use accessing a vessel percutaneously at a first depth.

The ultrasound probe 12 includes distal and proximal ends 30, 32, a distal surface 34, a side wall 36, a cable 38, and a connection feature 39. The distal surface 34 may be arranged to abut against an outer surface 6 of a tissue layer as shown in FIG. 5. The needle adjustment device 14 may be mounted to the side wall 36 and connected with a positive connection using the connection feature 39. The connection feature 39 may include various connection features, including, for example, a clamp, a press-fit or interference-fit connection, a snap-fit connection, a fastener, or a bonding agent such as an adhesive. While the connection feature 39 is shown as a position stop along the length of the side wall 36, the connection feature 39 may include other connection features that provide a positive connection with the needle adjustment device 14. The connection feature 39 may provide a releasable connection of the needle adjustment device 14 to the ultrasound probe 12. In some examples, the connection feature 39 may provide adjustability of the needle adjustment device 14 along a length of the ultrasound probe 12.

The cable 38 may provide an electrical connection with the monitor 18. In at least some examples, the ultrasound probe 12 may be electrically connected with the monitor 18 using a wireless connection. Typically, the monitor 18 is positioned in close proximity so the operator may view the monitor 18 while using the ultrasound probe 12. The ultrasound probe 12 and monitor 18 together may provide real-time images of the vessel and other features such as the needle member 16.

The needle adjustment device 14 may include a probe attachment member 20, an adjustment member 22, and a needle carrier 24. The probe attachment member 20 is connected to the ultrasound probe 12. The adjustment member 22 provides an adjustable connection between the probe attachment member 20 and the needle carrier 24. The needle carrier 24 may include features that provide a releasable connection to the needle member 16. In at least one example, a needle carrier 24 includes a cavity such as a pass through bore within which a portion of the needle member 16 is positioned. The needle carrier 24 may include a plurality of attachment or adjustment features that assist in holding the needle member 16 in a desired axial position relative to the needle adjustment device 14.

The probe attachment member 20 may include a probe bore 40, an attachment arm 42, and a plurality of length indicia 44. The probe bore 40 may be sized to receive at least a portion of the ultrasound probe 12. In one example, the probe bore 40 has a tapered construction that facilitates an interference fit connection between the ultrasound probe 12 and needle adjustment device 14. In other examples, the probe attachment member 20 is constructed to provide a snap-fit connection to the ultrasound probe 12. In one example, the probe attachment member 20 may include an opening along a length thereof that provides lateral access into the probe bore 40 for mounting the probe attachment member 20 laterally onto the ultrasound probe 12. In some arrangements, an attachment feature such as a fastener may extend through the probe attachment member 20 and into the probe bore 40 for contact with the ultrasound probe 12.

The length indicia 44 may be positioned on the attachment arm 42. The length indicia 44 may provide a visual indication of an axial position of the probe attachment member 20 relative to the adjustment member 22. In one example, the attachment arm 42 is insertable into the adjustment member 22. In other examples, the adjustment member 22 is insertable into a cavity of the probe attachment member 20 to provide adjustable axial and rotational movement therebetween. An interface between the attachment arm 42 and the adjustment member 22 may allow for rotational adjustability about a longitudinal axis of the attachment arm 42.

The adjustment member 22 includes an arm cavity 50, a pivot cavity 52, a length adjustment member 54, a plurality of first rotation members 56, a rotation fastener 58, a first fastener bore 60, and a plurality of angle indicia 62. The arm cavity 50 may be sized to receive the attachment arm 42 of the probe attachment member 20. The arm cavity 50 may include a generally rectangular cross-sectional shape to receive the generally rectangular cross-sectional shaped attachment arm 42. In other examples, other cross-sectional shapes are possible for the arm cavity 50 and the attachment arm 42 including, for example, a circular cross-sectional shape.

The pivot cavity 52 may be sized to receive a pivot portion of the needle carrier 24. The pivot cavity 52 may provide pivotal movement of the needle carrier 24 within a common plane P extending through the ultrasound probe 12, needle adjustment device 14, and needle member 16 (see FIG. 4). The planar arrangement of the ultrasound probe 12, needle adjustment device 14, and needle member 16 may provide improved visibility of the needle member 16 by the ultrasound probe during insertion of the needle member 16 into the tissue layer.

The length adjustment member 54 may operate to fix an axial position of the attachment arm 42 within the arm cavity 50. The length adjustment member 54 may include, for example, a fastener such as a set screw that extends through a side wall of the adjustment member 22 and into contact with the attachment arm 42 of the probe attachment member 20. Other types of adjustable connection features, such as a bracket, clip, or interference fit, may be used in place of the set screw shown in the figures.

The first rotation members 56 may be positioned within the pivot cavity 52. The first rotation members 56 may provide friction features that assist in holding the needle carrier 24 in a desired rotated position relative to the adjustment member 22. In one example, the first rotation members 56 include a plurality of ridges or protrusions extending radially outward from the first fastener bore 60 (see FIG. 2).

The rotation fastener 58 may extend through the first fastener bore 60 and provide a pivot axle about which the needle carrier 24 rotates. The rotation fastener 58 may include, for example, a bolt and nut assembly. Tightening the rotation fastener 58 may help maintain a rotated position of the needle carrier 24 relative to the adjustment member 22.

The angle indicia 62 may be positioned on an exterior surface of the adjustment member 22. The angle indicia 62 may provide a visual indicator to the operator of a rotated position of the needle carrier 24 relative to the adjustment member 22. The angle indicia 62 may include indicia positioned at certain angles, such as, for example, about every 2° to 5°, or about every 5° to 10°. The angle indicia 62 may include line segments as well as numbers and other symbols.

The needle carrier 24 includes a pivot member 70, a plurality of second rotation members 72, a second fastener bore 74, a needle bore 76, and a plurality of axial position members 78 (see FIG. 5). The needle carrier 24 may also include a plunger 79 (see FIG. 8), a distal stop surface 80, a needle outlet 82, and a marker 83 (see FIGS. 1 and 5). The pivot member 70 may be insertable into the pivot cavity 52. The second rotation member 72 may be mounted to an external surface of the pivot member 70 and may be arranged to interface with the first rotation members 56. The second rotation members 72 (see FIG. 2) may be arranged extending radially outward from the second fastener bore 74. The second rotation members 72 may be in the form of, for example, recesses, grooves or protrusions. The second rotation members 72 and first rotation members 56 may interface with each other to provide predetermined rotation steps (e.g., about 1° to 5° per step).

The needle bore 76 may include a plurality of axial position members 78 positioned along the length thereof. The needle bore 76 may be sized to receive a portion of the needle member 16 such as, for example, a base 90 as will be described below. The axial position members 78 may include a plurality of step features that interface with the base 90 of the needle member 16. In some arrangements, one or more biasing members 77 (see FIG. 6) may be positioned within the needle bore 76 to assist in holding the needle member 16 in a desired axial position along the length of the needle bore 76 by contact with one or more of the axial position members 78.

The distal stop surface 80 may provide a distal position stop for movement of the needle member 16 within the needle bore 76. The needle outlets 82 may be sized to receive a portion of needle member 16 (e.g., a needle 94, as described below).

The marker 83 may be positioned along an exterior surface of the needle carrier 24. The marker 83 may assist in providing a visual indication of a rotated position of the needle carrier 24 relative to the adjustment member 22. The marker 83 may align with one of the angle indicia 62 on the adjustment member 22 at each rotated position. In some arrangements, the marker 83 may be positioned on the needle carrier 24.

The plunger 79 may be used to advance the needle member 16 within the needle bore 76. In some arrangements, a portion of the needle member 16 (e.g., the base 90) may be sized to have at least a portion thereof always extending outside of the needle bore 76 while advancing the needle member 16 within the needle bore 76 towards the distal stop surface 80.

In some arrangements, the needle adjustment device 14 includes only the probe attachment member 20 and the needle carrier 24. The needle carrier 24 may include the arm cavity 50 such that the needle adjustment device 14 only provides a length adjustment. In other examples, the needle adjustment device 14 includes only a pivot adjustment of a needle carrier 24 relative to the probe attachment member 20 by providing the pivot cavity 52 at an end of the attachment arm 42.

The needle member 16 may include a base 90, a lip 92, and a needle 94 having a distal tip 96. The lip 92 may contact the axial position member 78 within the needle bore 76 to maintain an axial position of the needle member 16 within the needle carrier 24. The needle 94 may have any desired length, such as a length sufficient to access vessels at various depths D while the needle adjustment device 14 is positioned at any length adjusted position between the probe attachment member 20 and adjustment member 22, or at any range of rotated positions between the adjustment member 22 and needle carrier 24 for a given length adjustment. As mentioned above, the base 90 may have any desired size and shape. In one example, the base 90 has a length that provides exposure of at least a portion of the base 90 outside of the needle bore 76 at all positions of the needle member 16 within the needle carrier 24. In other arrangements, the base 90 may be completely positioned within the needle bore 76, and a plunger 79 is used to advance the needle member 16 within the needle bore 76 to each position defined by the axial position members 78.

Referring to FIG. 5, adjustability of the needle adjustment device 14 is shown in further detail. The length adjustment member 54 may be adjusted to permit relative length adjustment between the probe attachment member 20 and the adjustment member 22. Providing a length adjustment in the direction B as shown in FIG. 5 alters a length $L_1$ between the ultrasound probe 12 and the point of connection between the needle carrier 24 and the adjustment member 22 (i.e., the second fastener bore 74). After making the length adjustment in the direction B, the length adjustment member 54 may be operated again to fix the position of probe attachment member 20 relative to adjustment member 22.

The pivoted position of needle carrier 24 relative to adjustment member 22 may be adjusted by first loosening the rotation fastener 58, which permits relative movement between the first and second rotation members 56, 72. The needle carrier 24 is rotated relative to the adjustment member 22 to adjust a rotation angle $\alpha_1$ between a longitudinal axis $A_1$ of the ultrasound probe 12 and a longitudinal axis $A_2$ of the needle member 16 (see FIG. 5).

After locating a vessel 2 below an outer surface 6 using the ultrasound probe 12, the length $L_1$ may be adjusted to provide access to the vessel 2 with the needle member 16 for a fixed rotation angle $\alpha_1$ when the vessel 2 is at a given depth $D_1$. Alternatively, a fixed length $L_1$ may be maintained and the adjustment angle $\alpha_1$ may be altered in order to access the vessel 2 at the depth $D_1$. The needle placement assembly 10 may be rotated in a direction R into a position as shown in FIG. 5 such that the needle 94 is insertable at various angles $\alpha_1$ relative to an outer surface of the vessel 2. In other examples, the needle placement assembly 10 may be rotated 90° about a central axis $A_1$ so that the needle 94 is inserted an angle $\alpha_1$ relative to a length dimension of the vessel 2. The needle placement assembly 10 may be rotated about 180° about axis $A_1$ relative to the position shown in FIG. 5 to insert the needle member 16 into an opposite side of vessel 2.

Figure 6:
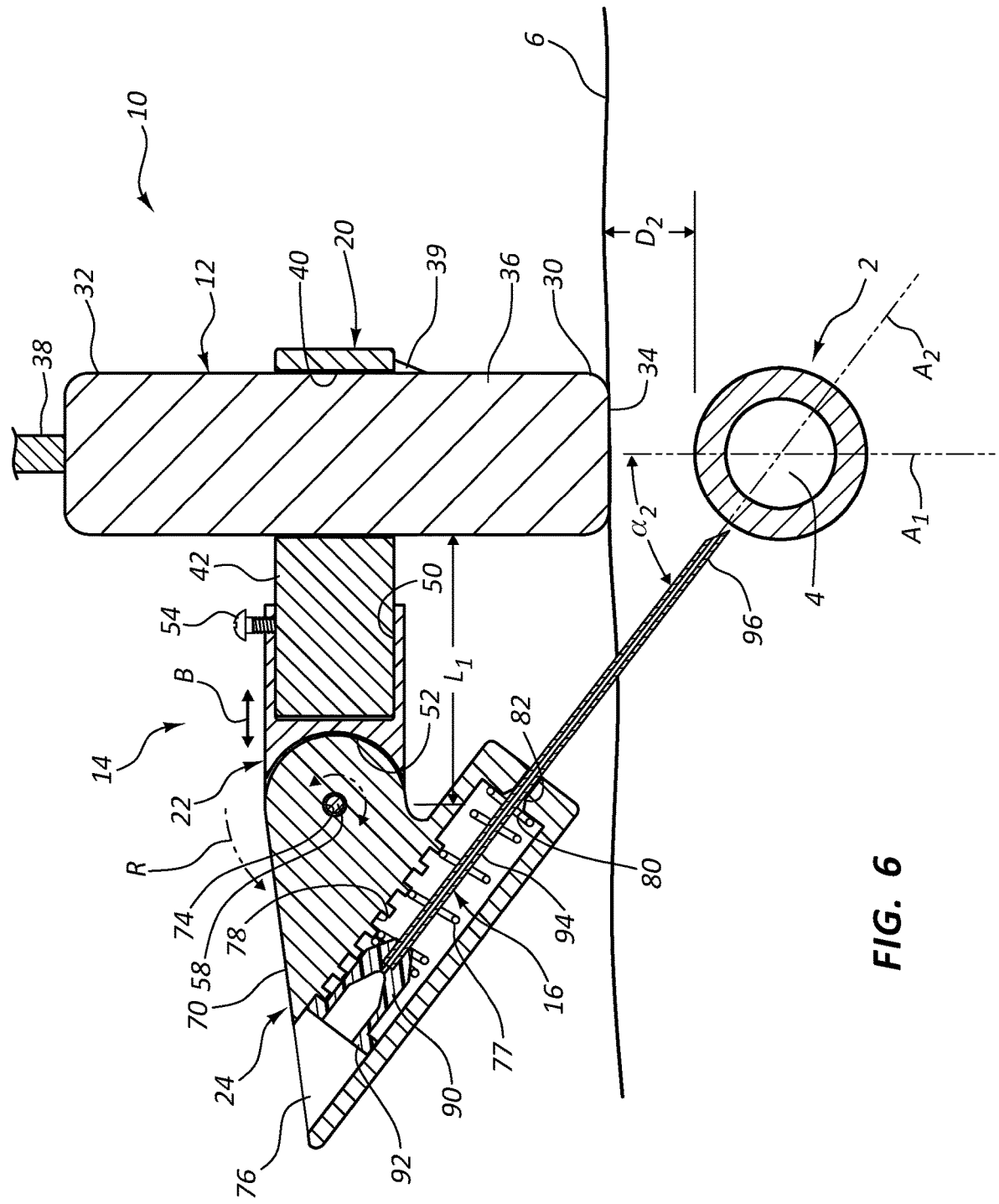
FIG. 6 is a cross-sectional view of the needle placement assembly of FIG. 1 with the needle adjustment device adjusted to provide access to a vessel percutaneously at a second depth.

FIG. 5 shows the vessel 2 positioned at a depth $D_1$ relative to the outer surface 6 of the tissue layer. The vessel 2 is accessed with the needle 94 with the needle adjustment device 14 having a length adjustment $L_1$ and providing an angle orientation of $a_1$. FIG. 6 shows the vessel 2 at a depth $D_2$, which is less than the depth $D_1$. The length adjustment is maintained at $L_1$ and the angle adjustment is adjusted to an angle $\alpha_2$, which is greater than $\alpha_1$. Alternatively, the length dimension may be adjusted to a length that is less than $L_1$ and the angle may be maintained at $\alpha_1$.

Figure 7:
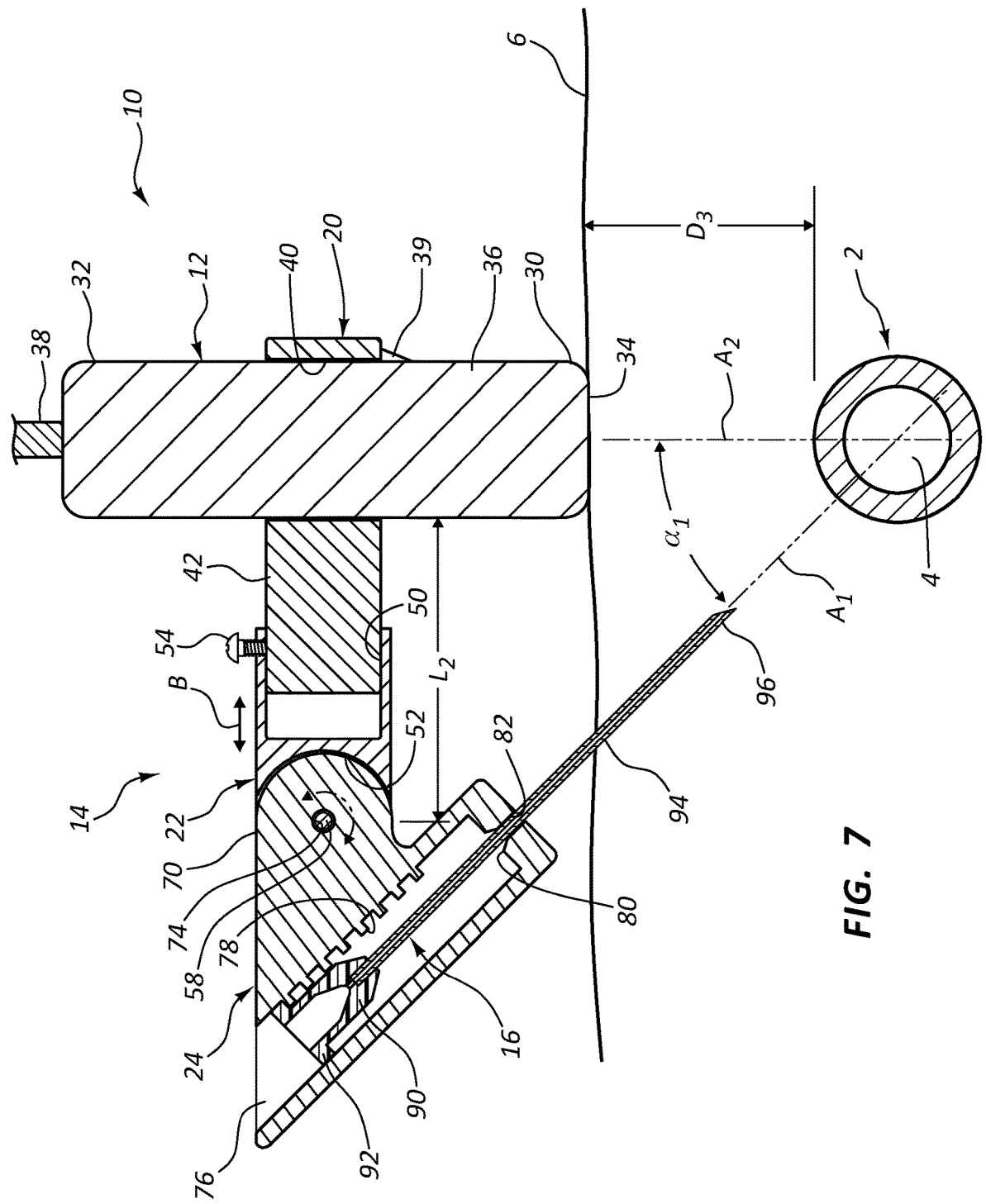
FIG. 7 is a cross-sectional view of the needle placement assembly of FIG. 1 with the needle adjustment device adjusted to provide access to a vessel percutaneously at a third depth.

FIG. 7 shows the vessel 2 positioned at a depth $D_3$. The angle may be maintained at $\alpha_1$ while the length L may be adjusted in the direction B to a length $L_2$, which is greater than the length $L_1$. Alternatively, the length may be maintained at $L_1$ and the angle $\alpha$ may be adjusted to be less than the angle $\alpha_1$.

When the needle adjustment device includes only one of the length adjustment or the rotation adjustment, it is possible to gain access to the vessel 2 with the needle 94, but there may be less control over the angle $\alpha$ at which the needle 94 is inserted to form a percutaneous puncture and gain access to an interior 4 of the vessel 2.

Figure 8:
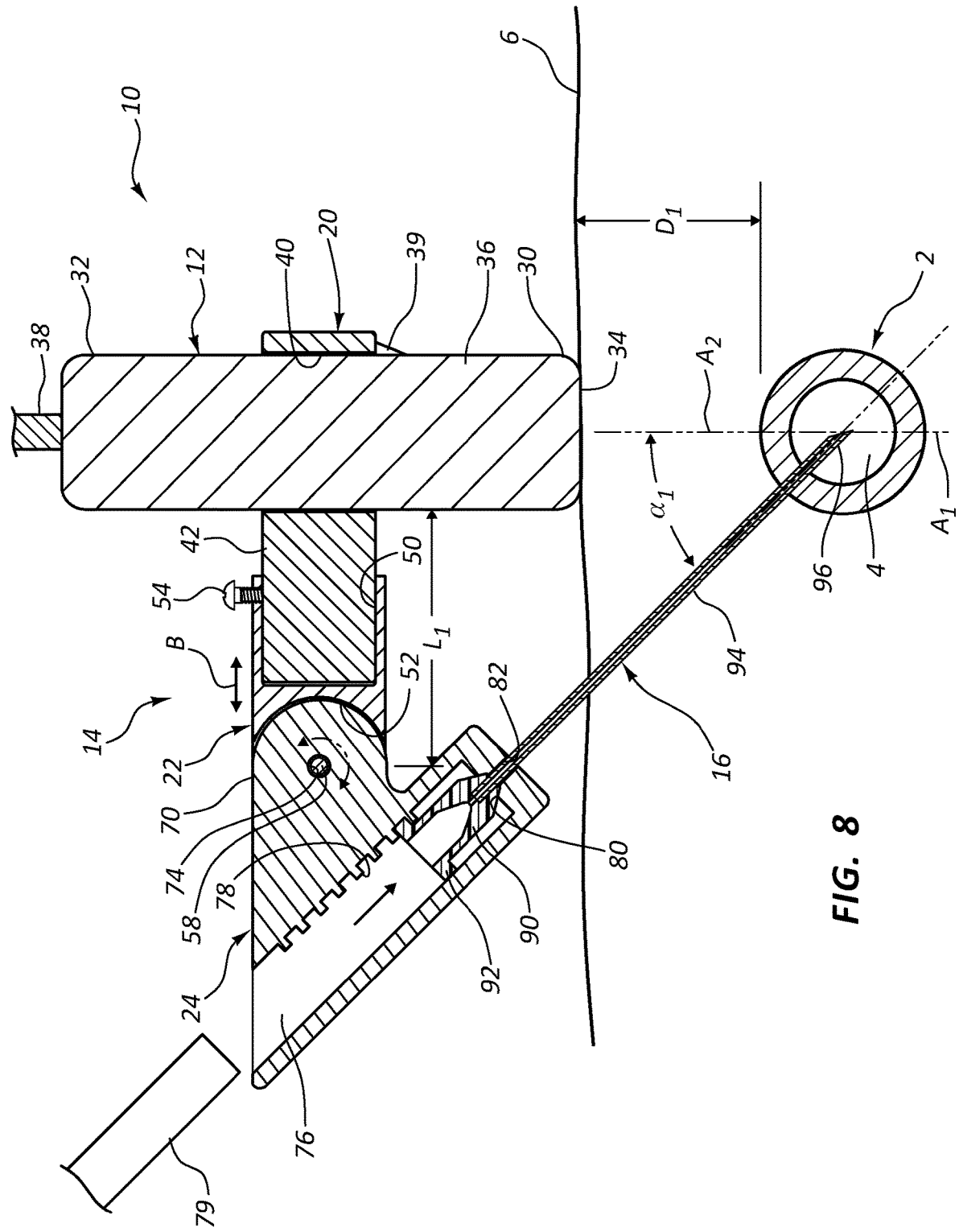
FIG. 8 is a cross-sectional view the needle placement assembly of FIG. 5 with a needle advanced into the vessel.

After the vessel 2 has been located using the ultrasound probe 12 and the axis $A_1$ of the ultrasound probe 12 is aligned centrally with a central axis of the vessel 2, the needle adjustment device 14 is adjusted to align the needle 94 with the vessel 2 and the needle 94 is advanced toward the vessel 2. The operator may view on the monitor 18 a position of the needle 94 as it is advanced towards the vessel 2. A plunger 79 may be used to advance the needle member 16 through the needle bore 76 of the needle carrier 24 until the distal tip 96 of the needle 94 advances into the vessel lumen 4 as shown in FIG. 8.

Figure 9:
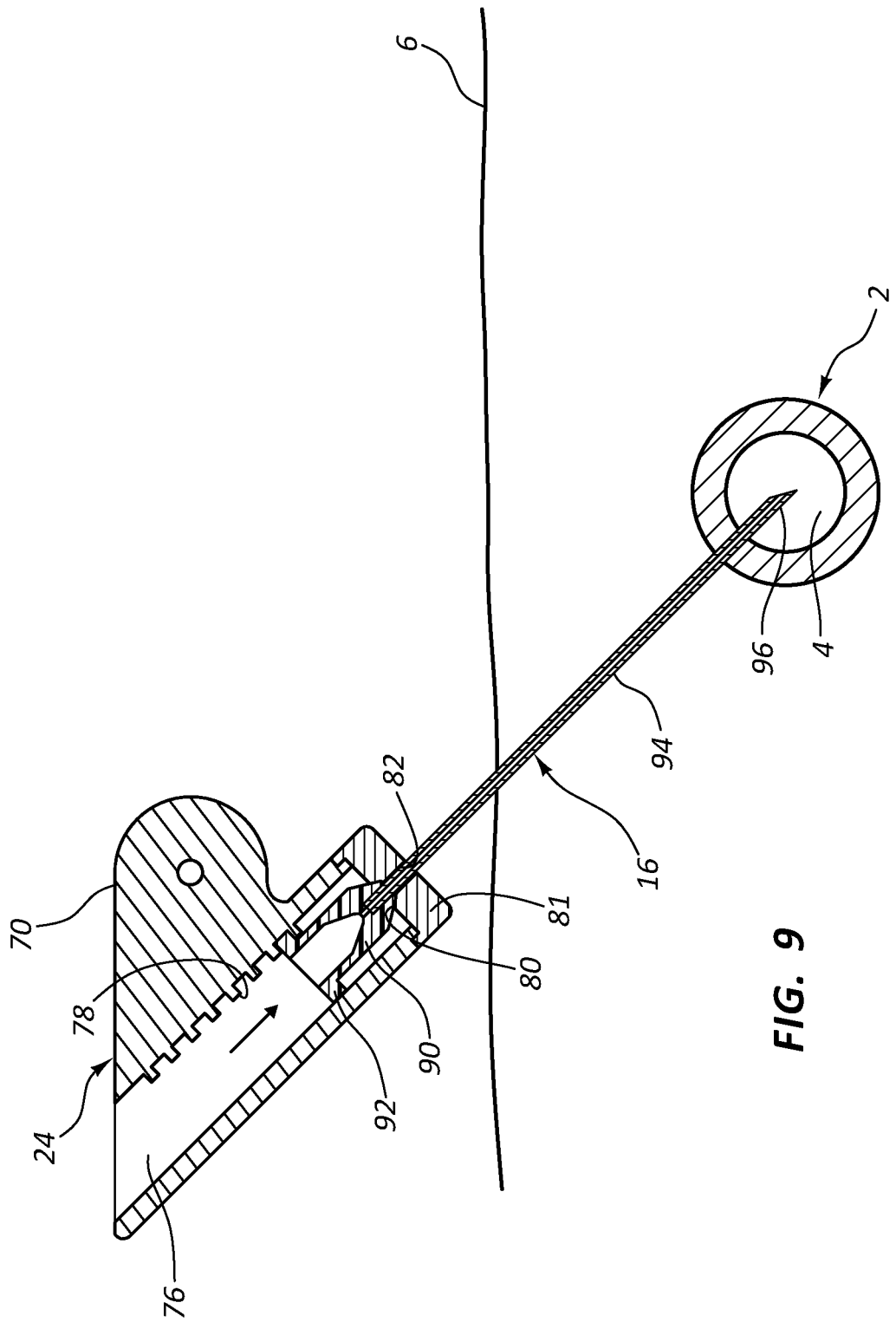
FIG. 9 shows a portion of the needle placement assembly of FIG. 8 removed and the needle remaining positioned in the vessel.
Figure 10:
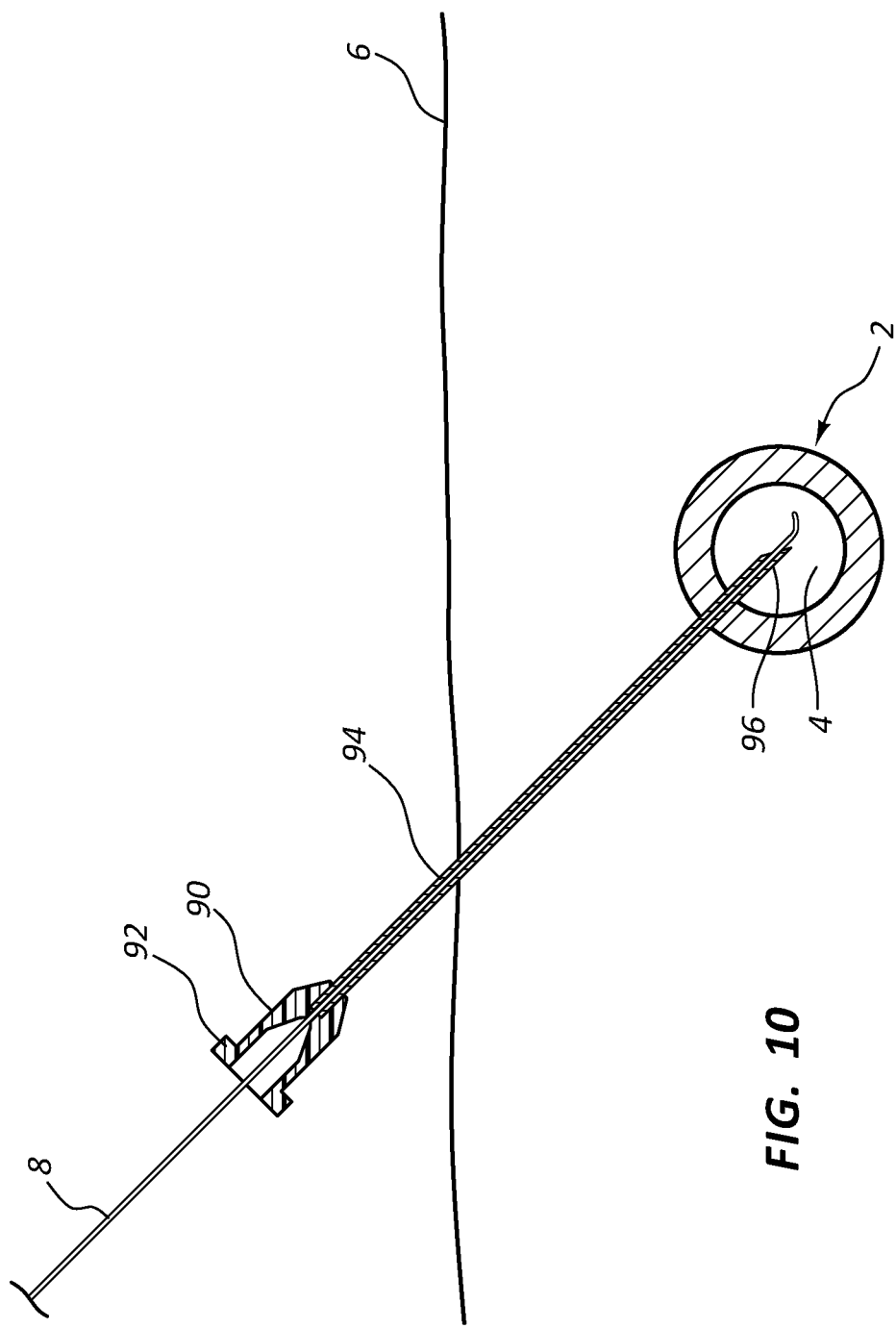
FIG. 10 shows the needle placement device removed with the needle remaining positioned in the vessel and a guidewire advanced through the needle and into the vessel.

Once the vessel 2 is accessed with the needle 94, portions of the needle placement assembly 10 may be detached from each other. For example, the ultrasound probe 12 may be detached from the needle adjustment device 14. In one example, the probe attachment member 20 and needle adjustment member 22 are detached from the needle carrier 24, and the needle member 16 remains positioned within the needle carrier 24. In still further examples, the ultrasound probe 12 and needle adjustment device 14 are completely detached from the needle member 16. In one example, the needle carrier 24 includes a break away portion 81 at a distal end thereof that permits removal of the needle member 16 from the needle bore 76 in a distal direction (see FIG. 9). The break away portion 81 may include a detachable cap or other feature at a distal end of the needle carrier 24 that provides access into the needle bore 76. A guidewire 8 may be advanced through the needle member 16 and into the vessel lumen 4 whether the needle member 16 remains positioned in connection with the needle carrier 24 or is removed from the needle adjustment device 14 (see FIG. 10). The guidewire 8 provides access into the vessel lumen 4 after removal of the needle member 16 from the vessel 2.

Figure 11:
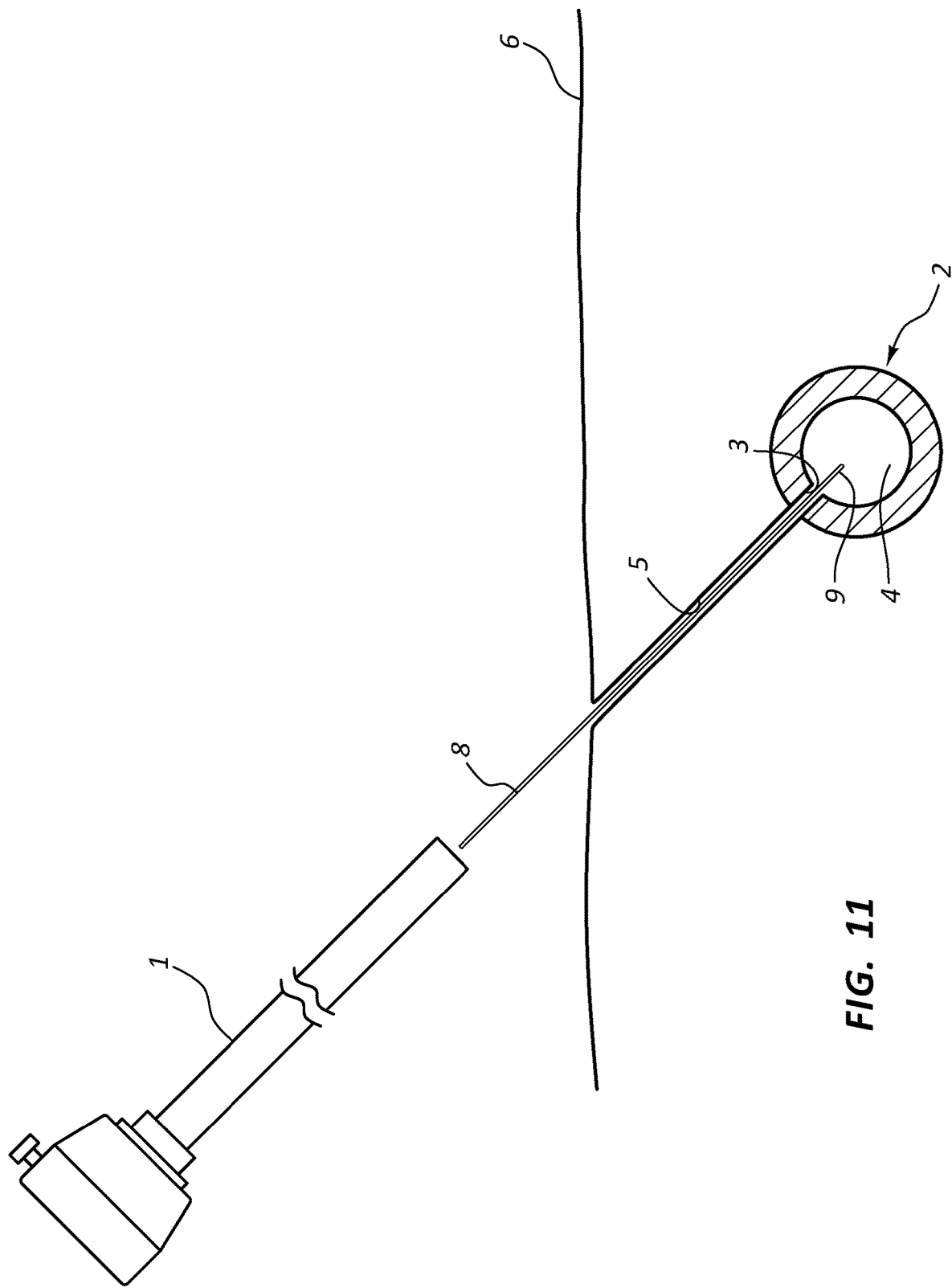
FIG. 11 shows the needle removed from the guidewire and another device arranged for advancement over the guidewire.

FIG. 11 shows the needle member 16 removed from the vessel 2 and tissue layer to leave behind a tissue tract 5 (also referred to as a percutaneous puncture) and a vessel puncture 3. Another device 1 such as, for example, a dilator, insertion sheath, treatment device, or puncture closure device may be advanced along the guidewire 8, through the tissue tract 5, through the vessel puncture 3, and into the vessel lumen 4 and then operated as part of treating the patient.

Figure 12:
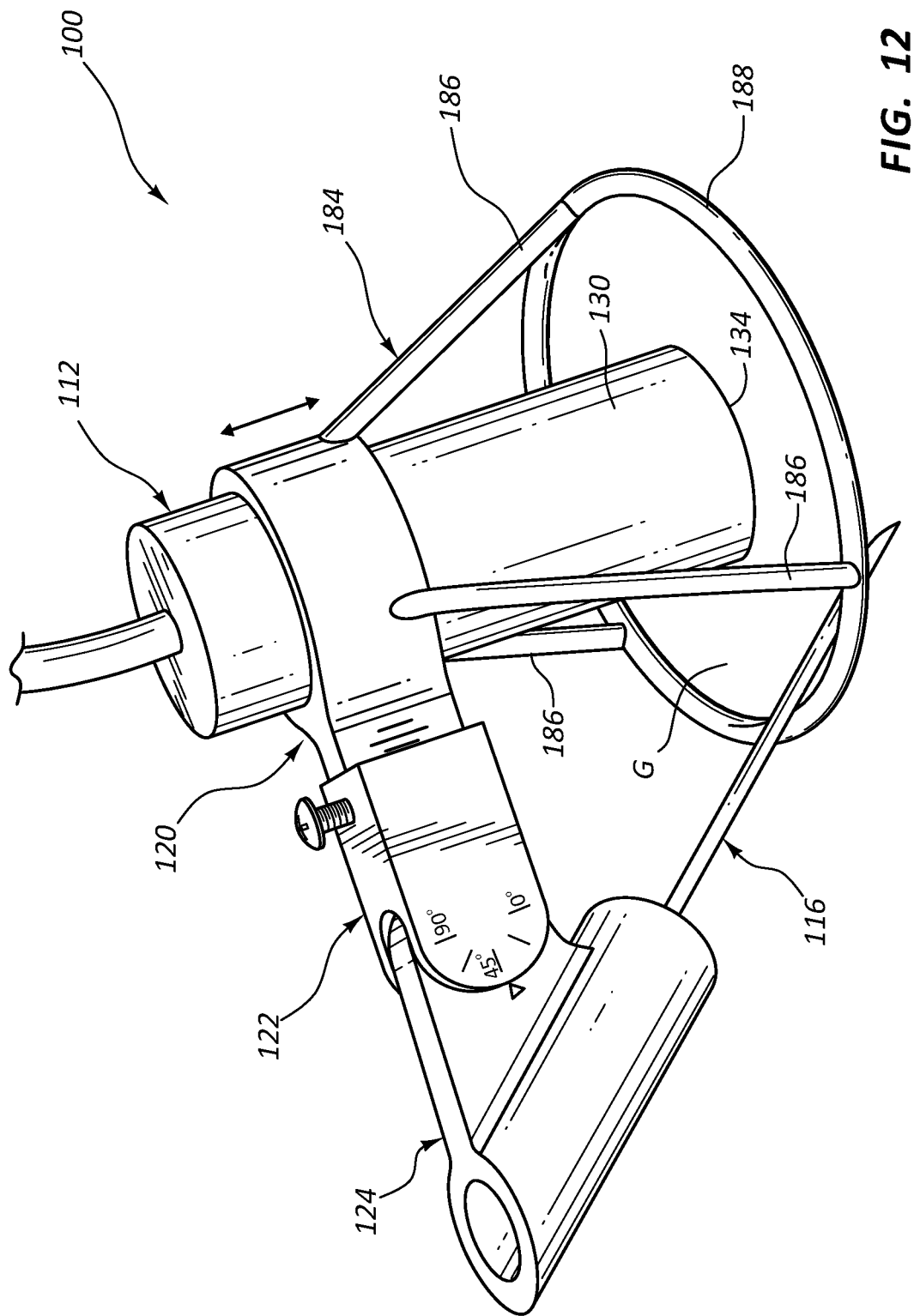
FIG. 12 is a perspective view of another example needle placement assembly including an integrally formed stabilization ring in accordance with the present disclosure.
Figure 13:
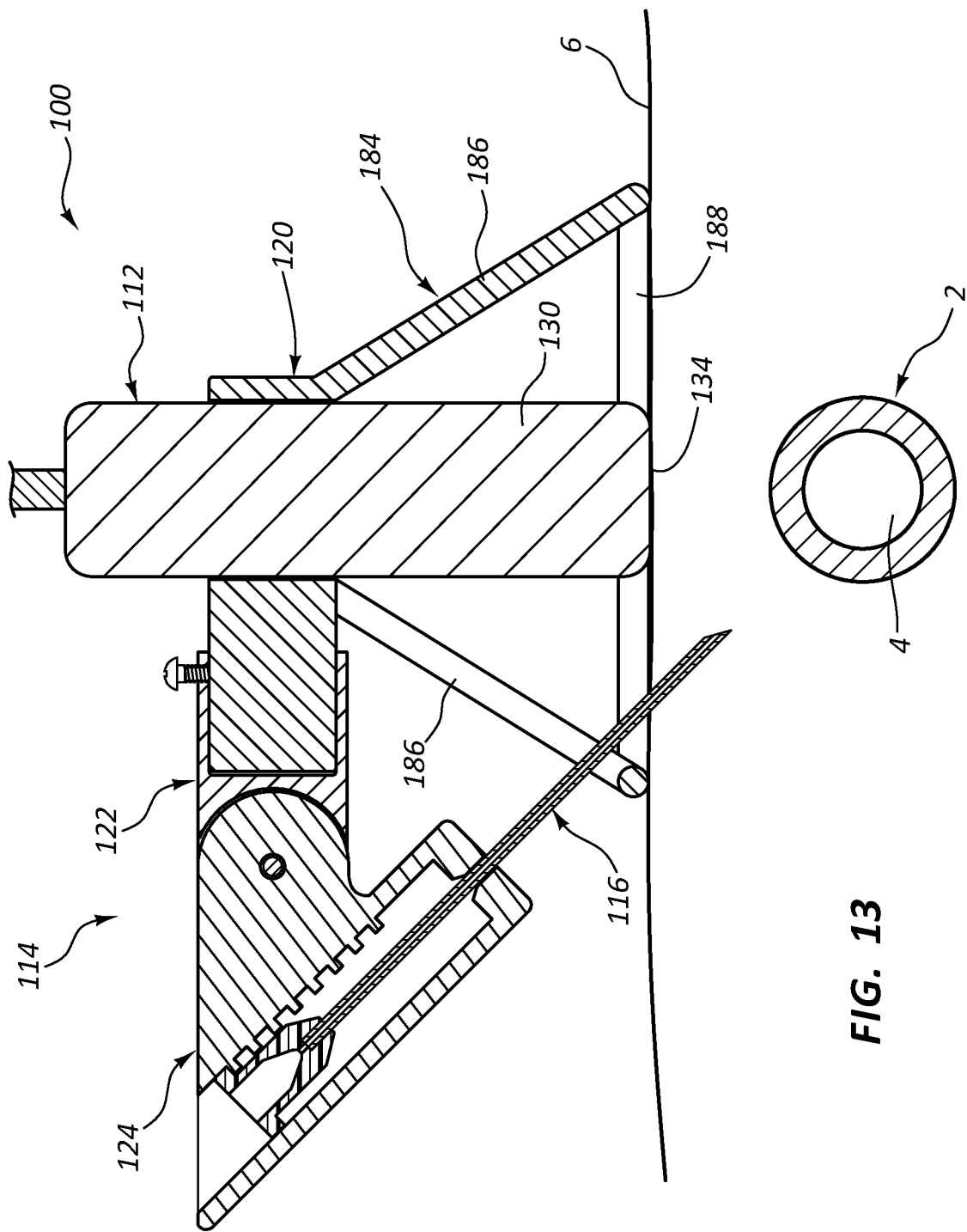
FIG. 13 is a cross-sectional view of the needle placement assembly of FIG. 12 arranged for accessing a vessel percutaneously.

Referring now to FIGS. 12 and 13, another example needle placement assembly 100 having a stabilization member 184 is shown. The needle placement assembly 100 includes an ultrasound probe 112, a needle adjustment device 114, a needle member 116, and a stabilization member 184 (also referred to as a stabilizing ring). The needle adjustment device 114 includes a probe attachment member 120, an adjustment member 122, and a needle carrier 124. The stabilization member 184 may extend from and be mounted to the needle adjustment device 114. In some examples, the stabilization member 184 is integrally formed as a single piece with a portion of with the needle adjustment device 114, such as the probe attachment member 120. In one example, the stabilization member 184 is mounted directly to the probe attachment member 120. The stabilization member 184 may extend to the distal end 130 of the ultrasound probe so that the stabilization member 184 is also in contact with the outer skin surface when the distal end 130 of the ultrasound probe is in contact with the outer surface 6.

The stabilization member 184 may include a plurality of support arms 186 and a ring member 188. The ring member 188 may include a high friction surface that assists in maintaining a position of the stabilization member 184 on an outer surface of a tissue layer. The support arms 186 may provide a connection between the ring member 188 and the needle adjustment device 114.

The support arms 186 may be spaced apart circumferentially around the ring member 188. A plurality of gaps G may be formed between the support arms 186. The gaps B may provide visualization of the probe distal end 30 while the stabilization member 184 is in use. The needle member 116 may extend through the gaps G when moving into contact with the tissue layer. In other examples, the needle member 116 is inserted into the tissue layer outside of the ring member 188.

FIG. 13 shows the ring member 188 and a distal surface 134 of the ultrasound probe 112 in contact with the outer surface 6 of the tissue layer. The needle adjustment device 114 is adjustable to align the needle member 116 with the vessel 2 once the vessel 2 has been located using the ultrasound probe 112. Thereafter, the needle member 116 is advanced through the tissue layer and into the vessel lumen 4. The stabilization member 184 helps maintain the ultrasound probe 112 in a fixed orientation while limiting movement of the ultrasound probe 112 along the outer surface 6 of the tissue layer, particularly while advancing the needle member 116 through the tissue layer and into the vessel 2.

Figure 14:
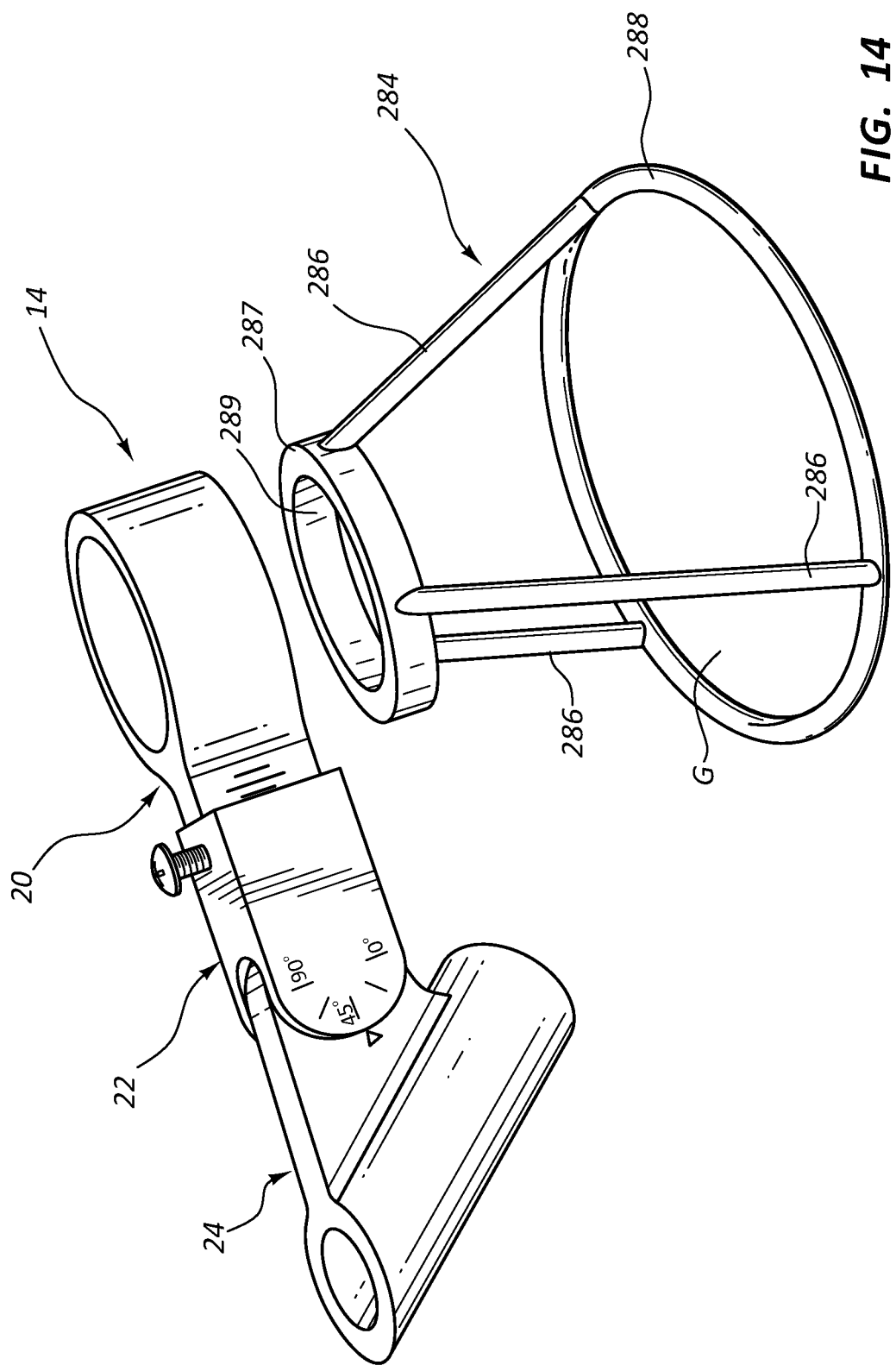
FIG. 14 is a perspective view of another example needle placement assembly including a stabilization ring as a separate piece from the needle adjustment device in accordance with the present disclosure.

Referring to FIG. 14, another example stabilization member 284 is shown as a separate device from the needle adjustment device 14. The stabilization member 284 may include a plurality of support arms 286, a ring member 288, and a probe attachment member 287 having a probe bore 289 sized to receive the ultrasound probe 12. The stabilization member 284 may be movable axially along a length of the ultrasound probe 12. In one example, the ultrasound probe 12 is operable to locate a vessel below the outer surface 6 of the tissue layer. Thereafter, the stabilization member 284 is advanced distally along a length of the ultrasound probe 12 and into contact with the outer surface 6 of the tissue layer. An axial position of the stabilization member 284 may then be fixed relative to the ultrasound probe 12 to help maintain the ultrasound probe 12 in a fixed orientation and position while the needle member 16 is advanced through the tissue layer and into the vessel 2.

The stabilization member 284 may be moveable relative to the needle adjustment device 14 and the ultrasound probe 12. The stabilization member 284 may include connection features that realeasably secure the stabilization member 284 at any desired location along the length of the ultrasound probe 12. In some examples, the ultrasound probe 12 includes attachment features such as position stops, fasteners and the like that control axial movement of the stabilization member 284 relative to the ultrasound probe 12.

The ring members 188, 288 disclosed herein may include a high friction surface comprising, for example, a high friction material or a high friction construction. For example, the ring member 188, 288 may include a coating of silicone, adhesive, or other high friction material. Alternatively, the ring member 188, 288 may include a plurality of ridges, grooves, dimples, or other structure that provide increased surface friction.

One advantage of the example needle adjustment device and other features of the needle placement assemblies disclosed herein may relate to providing for a central needle puncture or access into a body cavity (e.g., a vessel lumen). Providing a central puncture or access may be one factor in achieving closure success when using vascular closure devices after treating the patient through the vessel puncture. The use of an ultrasound probe to locate a vessel and then guide a puncture device such as a needle through a tissue layer and into a vessel lumen may be particularly useful. The needle adjustment features disclosed herein may provide improved standardization of the angle in which the puncture is made through the tissue layer and into the vessel for any number of different vessel depths.

Furthermore, the needle adjustment device may provide alignment of the ultrasound probe in the same plane as the needle insertion. This co-planar arrangement may provide improved visualization of the needle or other puncture device during advancement through the tissue layer and into the vessel. The integrated nature of the needle adjustment device and its function of coupling the needle member to an ultrasound probe may provide a simplified construction and easier operation by eliminating at least some components typically needed in order to control the insertion angle of the puncture device (e.g., needle) relative to the ultrasound probe for vessels positioned at varying depths.

Various features or combinations of features in accordance with the present disclosure may provide other advantages. An example device in accordance with the present disclosure may provide attachment of a needle adjustment device to an ultrasound or sonar probe to aid in puncture of a vessel percutaneously. The needle adjustment device may include a sliding needle guide that positions a needle at any desired angle (e.g., a 45° angle). The sliding needle guide may include a spring assist or a lock feature that helps hold the needle member in a fixed axial position when advancing the needle member through a tissue layer into the vessel. In at least some arrangements, the needle member may be selectively attached and detached from the needle adjustment device. The needle may be detached with a portion of the sliding needle guide from remaining portions of the needle adjustment device to maintain a position of the needle member in the vessel. The sliding needle guide may have an adjustable angle feature and may have a spacing between the ultrasound probe and the needle guide that is also adjustable. The needle adjustment device may be secured to an ultrasound probe using a variety of attachment features including, for example, a snap-fit connection, a press-fit connection, or other attachment feature or mechanism. The needle adjustment device may be provided as an assembly with an ultrasound probe and a needle member. Furthermore, a monitor or display may be used in combination with the ultrasound probe to provide visualization of the images collected by the ultrasound probe.

As mentioned above, the sliding needle guide may provide a lateral adjustment relative to the ultrasound probe to account for varying depths of the vessel relative to an outer tissue surface while maintaining a fixed angle of insertion for the needle member. The needle adjustment device may include various lateral adjustment markings (e.g., indicia) to indicate different angles for the puncture. An example method may incorporate the housing of the ultrasound probe or sonar probe and needle adjustment device into one molded part.

The sliding needle guide may comprise a disposable portion of the needle adjustment device, whereas remaining portions of the needle adjustment device may be reusable or may be integrally formed with features of the ultrasound probe. A stabilization member may provide stabilization to help maintain an orientation and position of the ultrasound probe during insertion of the needle member through the tissue layer into the vessel. The stabilization feature may limit rotation and other movement of the ultrasound probe during puncture. The stabilization member may include a base having a high friction surface that assists in maintaining a position of the ultrasound probe along an outer surface of the tissue layer. The stabilization member may be retractable relative to the ultrasound probe.

The preceding description has been presented only to illustrate and describe exemplary embodiments of the invention. It is not intended to be exhaustive or to limit the invention to any precise form disclosed. Many modifications and variations are possible in light of the above teaching. It is intended that the scope of the invention be defined by the following claims.

What is claimed is:

1. A tissue puncture assembly, comprising:
    an ultrasound probe having a probe end arranged to contact a tissue surface, the ultrasound probe being operable to determine a depth of a body cavity positioned below the tissue surface;
    a tissue puncture device configured to penetrate the tissue surface to gain access to the body cavity, the tissue puncture device comprising a needle carrier, the needle carrier having a bore including a first side and a second side opposite each other, the needle carrier having a plurality of position members positioned in the bore and formed along the length of an interior of the bore, wherein a needle is retainable along the bore at a plurality of axial positions by the plurality of position members, the plurality of position members being positioned on the first side of the bore, the second side of the bore being smooth;
    an adjustment device having a longitudinal axis, a length adjustment member, a first end comprising an attachment arm mounted to the ultrasound probe, and a second end comprising an adjustment member mounted to the tissue puncture device, the attachment arm being positioned within the adjustment member, the adjustment device being operable to adjust an orientation of the tissue puncture device relative to the ultrasound probe, and having a variable length along the longitudinal axis between the first end and the second end by adjustable axial movement of the attachment arm relative to the adjustment member, the length adjustment member contacting the attachment arm and the adjustment member, the length adjustment member extending through a side wall of the adjustment member.

2. The tissue puncture assembly of claim 1, wherein the adjustment device is configured to vary a distance between the ultrasound probe and the tissue puncture device.

3. The tissue puncture assembly of claim 1, wherein the adjustment device includes a pivot adjustment portion operable to change an angle or orientation of the tissue puncture device relative to the ultrasound probe.

4. The tissue puncture assembly of claim 1, further comprising a display configured to show a position of the ultrasound probe relative to the body cavity.

5. The tissue puncture assembly of claim 1, wherein the tissue puncture device comprises a hub and a puncture member mounted to the hub, the hub being adjustably mounted to the adjustment device.

6. The tissue puncture assembly of claim 1, further comprising a stabilizing member extending radially outward from the ultrasound probe and being arranged to contact the tissue surface.

7. The tissue puncture assembly of claim 6, wherein the stabilizing member comprises a circular shaped ring portion arranged to contact the tissue surface.

8. The tissue puncture assembly of claim 6, wherein the stabilizing member is adjustable along a length of the ultrasound probe.

9. The tissue puncture assembly of claim 1, wherein the ultrasound probe, the tissue puncture device, and the adjustment device are arranged in a common plane.

10. A needle placement assembly, comprising:
an ultrasound probe;
a needle having a base;
a needle adjustment device having a longitudinal axis between first and second ends, a probe attachment member positioned at the first end and configured to connect to the ultrasound probe, and a needle carrier positioned at the second end and configured to connect to the needle, the probe attachment member being positioned within the needle carrier, the needle adjustment device having a variable length along the longitudinal axis between the first and second ends and being configured to adjust a position of the needle relative to the ultrasound probe by adjustable axial movement of the probe attachment member relative to the needle carrier, the needle carrier having a bore and a plurality of step features formed along the length of an interior of the bore, wherein the needle is retainable in the bore by at least one of the plurality of step features interfacing with the base of the needle, wherein the base of the needle interfaces with the plurality of step features on only one side of the base at a time;
a length adjustment member contacting the probe attachment member and the needle carrier, the length adjustment member extending through a side wall of the needle carrier;
a plurality of length indicia positioned between the probe attachment member and the needle carrier, the plurality of length indicia being configured to visually indicate an axial position of the probe attachment member relative to the needle carrier.

11. The needle placement assembly of claim 10, wherein the needle is movable relative to the needle carrier and is insertable through a tissue layer against which the ultrasound probe abuts.

12. The needle placement assembly of claim 10, wherein the ultrasound probe is configured to abut against a tissue layer and locate a vessel positioned below the tissue layer, the needle being insertable through the tissue layer and vessel to access a lumen of the vessel.

13. The needle placement assembly of claim 12, further comprising a display showing images of the vessel generated by the ultrasound probe.

14. The needle placement assembly of claim 10, wherein the needle adjustment device includes a pivot adjustment portion.

15. A method of accessing a vessel percutaneously, comprising:
providing a needle placement assembly having an ultrasound probe, a needle adjustment device, a length adjustment member, and a needle, the needle adjustment device having a longitudinal axis extending between first and second ends, the needle adjustment device having a variable length along the longitudinal axis between the first and second ends, the first end comprising an attachment arm, the attachment arm having a plurality of length indicia, the second end comprising an adjustment member, the attachment arm being positioned within the adjustment member and being adjustably axially movable relative to the adjustment member, the ultrasound probe being mounted to the first end and the needle being mounted to the second end, the length adjustment member contacting the attachment arm and the adjustment member, the length adjustment member extending through a side wall of the adjustment member;
contacting the ultrasound probe against a tissue layer;
determining a location of the vessel below the tissue layer;
adjusting the needle adjustment device to alter an orientation of the needle relative to the ultrasound probe, wherein a position of the adjustment member is adjusted relative to the plurality of length indicia;
advancing the needle through the tissue layer and into the vessel by advancing the needle to one of a plurality of axial positions in a bore in the needle adjustment device, wherein the needle is retained in the one of the plurality of axial positions by at least one of a plurality of step features formed along the length of an interior of the bore, the plurality of step features being spaced along a first side of the bore, the first side being opposite a second side of the bore, the second side of the bore being smooth relative to the first side.

16. The method of claim 15, wherein determining the location of the vessel includes displaying images of the vessel and tissue layer on a display screen.

17. The method of claim 15, wherein adjusting the needle adjustment device includes adjusting at least one of a length and a rotated position of the needle adjustment device.

18. The method of claim 15, wherein the needle adjustment device includes a probe attachment member connected to the ultrasound probe, a needle carrier connected to the needle, and the adjustment member, and adjusting the needle adjustment device includes adjusting at least one of a distance and a rotated position of the probe attachment member relative to the needle carrier with the adjustment member.

19. The method of claim 15, further comprising providing a stabilization ring, mounting the stabilization ring to one of the ultrasound probe and the needle adjustment device, and contacting the stabilization ring against the tissue layer after determining a location of the vessel.

* * * * *